United States Patent
Rudolph et al.

(10) Patent No.: US 6,462,017 B1
(45) Date of Patent: Oct. 8, 2002

(54) METHOD OF REDUCING SIDE EFFECTS OF CHEMOTHERAPY IN CANCER PATIENTS

(75) Inventors: Alfred R. Rudolph, Los Altos Hills, CA (US); Vincent Chung-Ying Tam, Hong Kong (HK); Maggie Jie Quan, Shanghai (CN)

(73) Assignee: SciClone Pharmaceuticals, Inc., San Mateo, CA (US)

( * ) Notice: Subject to any disclaimer, the term of this patent is extended or adjusted under 35 U.S.C. 154(b) by 0 days.

(21) Appl. No.: 09/561,917

(22) Filed: May 1, 2000

(51) Int. Cl.$^7$ ............................................. A01N 37/18
(52) U.S. Cl. .............................. 514/2; 514/2; 514/12; 514/21; 514/274; 514/772.3; 424/26; 424/78.37; 424/85.7; 530/324; 530/326; 530/334; 435/7.1; 435/7.9; 528/398
(58) Field of Search ................................. 530/324, 326, 530/334; 435/7.1, 7.9; 514/274, 2, 12, 21, 772.3; 424/26, 78.37, 85.7; 528/396

(56) References Cited

U.S. PATENT DOCUMENTS

| | | | |
|---|---|---|---|
| 5,273,963 A | 12/1993 | Moody | 512/12 |
| 5,861,406 A * | 1/1999 | Wehrmann | 514/274 |

OTHER PUBLICATIONS

Garaci et al., European Journal of Cancer, vol. 31A, pp. 2403–2405, 1995.*

Garaci et al., Mechanisms of Ageing and Development, vol. 96, pp. 103–116, 1997.*

Salvati et al., Anticancer Research, vol. 16, pp. 1001–1004, 1996.*

E. Garaci et al., "Sequential Chemoimmunotherapy for Advanced Non–Small Cell Lung Cancer Using Cisplatin, Etoposide, Thymosin–Alpha1 and Interferon–Alpha 2A", European Journal of Cancer, 1995, pp. 2403–2405, vol.31A(13/14), Pergamon Press, Oxford, Great Britain.

H. Ishitsuka et al., "Efficacy of Thymosin Alpha 1 in Animal Models" Thymic Hormones and Lymphokines (PAP. Annu. Symp. Health Sci., 3rd, 1984, pp. 425–438, New York, NY, USA.

G. Silecchia et al., "Efficacy of Repeated Cycles of Chemo–Immunotherapy with Thymosin Alpha 1 and Interluekin–2 after Intraperitoneal 5–Fluorouracil Delivery", Cancer Immunology and Immunotherapy, 1999, pp. 172–178, vol. 48, Berlin, Federal Republic of Germany.

F. Salvati et al., "Combined Treatment with Thymosin–Alpha 1 and Low–Dose Interferon–Alpha after Ifosfamide in Non–Small Cell Lung Cancer: A Phase–II Controlled Trial", Anticancer Research, Helenic Anticancer Institute, 1996, pp. 1001–1004, vol. 16(2), Athens, Greece.

Y. Ohta et al., "Thymosin Alpha 1 Exerts Protective Effect Against the 5–FU Induced Bone Marrow Toxicity", Int'l Journal of Immunopharmacology, 1985, pp. 761–768, vol. 7(5), Elmsford, NY, USA.

Calvo, J.R. et al., "Interaction of Thymic Peptide Thymosin $\alpha_1$ with Vasoactive Intestinal Peptide (VIP) Receptors" Bioscience Reports, vol. 6(8):727–733 (1986).

Calvo, J.R. et al., "Interaction of Thymic Peptide Thymosin $\alpha_1$ with Vasoactive Intestinal Peptide (VIP) Receptors in Rat Intestinal Epithelial Cells: Comparison with PHI and Secretin" Gen'l Pharmac., vol. 20(4):503–505 (1989).

Pozo, D. et al., "Thymosin $\alpha$1 Interacts with the VIP receptor–effector system in rat and mouse immunocompetent cells" Immunopharmacology 34:113–123 (1996).

* cited by examiner

Primary Examiner—Karen Cochrane Carlson
Assistant Examiner—Hope A. Robinson
(74) Attorney, Agent, or Firm—Rothwell, Figg, Ernst & Manbeck

(57) ABSTRACT

A method for reducing the severity of chemotherapy side effects in cancer patients by administering thymosin $\alpha_1$ in conjunction with the administration of a chemotherapy agent to the patient. As a result of the reduction of post-chemotherapy side effects, patients experience an increase in the quality of life.

15 Claims, No Drawings

METHOD OF REDUCING SIDE EFFECTS OF CHEMOTHERAPY IN CANCER PATIENTS

FIELD OF THE INVENTION

The present invention relates to improved treatment of cancer in animals, including humans, by reducing the side effects of chemotherapy.

BACKGROUND OF THE INVENTION

Cancers are a leading cause of death in animals and humans. The leading cancer therapies today are surgery, radiation and chemotherapy. In spite of advances in the field of cancer treatment, each of these known therapies has serious side effects. For example, surgery disfigures the patient or interferes with normal bodily functions. Chemotherapy or radiation therapies cause patients to experience acute debilitating symptoms including nausea, vomiting, diarrhea, hypersensitivity to light, hair loss, etc. The side effects of these cytotoxic compounds frequently limit the frequency and dosage at which they can be administered.

Chemotherapeutic agents have been found useful in treating cancer in humans. Broadly classified as antineoplastics, chemotherapeutic agents found to be of assistance in the suppression of tumors include but are not limited to alkyleting agents (e.g., nitrogen mustards), antimetabolites (e.G., pyrimidine analogs), radioactve isotopes (e.g., phosphorous and iodine), hormones (e.g., estrogens and adrenocorticosteroids), miscellaneous agents (e.g., substituted ureas) and natural products (e.g., vinca alkyloids and antibiotics). Although the preceding compounds are not curative agents, they are widely recognized in the medical profession as useful in the suppression, palliation, retardation and control of malignant tumors. While these compounds have been found to be effective and are in general clinical use as antiproliferative agents, there are well recognized drawbacks associated with their administration. The alkylating agents have marked cytotoxic action and the ability of these drugs to interfere with normal mitosis and cell division can be lethal. The antimetabolites can lead to anorexia, progressive weight loss, depression, and coma. Prolonged administration of antimetabolites can result in serious changes in bone marrow. Both the alkylating agents and the antimetabolites generally have a depressive effect on the immunosuppressive system. Prolonged administration of natural products such as vinca alkyloids can also result in bone marrow depression. Hydroxy urea and other chemically derived agents can lead to rapid reduction in levels of adrenocorticosteroids and their metabolites. The administration of hormonal compounds or radioactive isotopes is also undesireable from the viewpoint of inflicting damage on the immunosuppressive system and thereby disabling the body's defenses against common infections. In most instances, it would be preferable to employ a chemotherapeutic agent which is effective in controlling, retarding, or suppressing the growth of malignant tumors while simultaneously acting to stimulate the patient's immune system.

SUMMARY OF THE INVENTION

In accordance with the present invention, a method is provided in which the side effects of chemotherapy in cancer patients are reduced by administering thymosin $\alpha_1$ ("T$\alpha_1$") in conjunction with the administration of the chemotherapy agent to the patient. The reduction in the severity of post-chemotherapy side effects increases the quality of life experienced by patients receiving chemotherapy.

DETAILED DESCRIPTION OF THE INVENTION

It is known that the thymus produces a family of polypeptides termed thymosin and perhaps several other thymic hormones and/or factors which play an important role in the maturation, differentiation and function of T-cells. Thymosin has been found to induce T-cell differentiation and enhance immunological functions in genetically athymic mice, in adult thymectisized mice and in NZB mice with severe autoimmune reactions, in tumor bearing mice and in mice with casein-induced amyloidosis.

Thymosin $\alpha_1$, an acidic polypeptide isolated from thymosin fraction 5 is an immunomodulator that acts primarily by enhancing T-cell function and also has been shown to have direct anti-cancer effects. Thymosin $\alpha_1$ has been found to stimulate T-cell maturation, differentiation and function.

It has been previously documented that thymosin $\alpha_1$ reduces the incidence and severity of post-chemotherapy infections. It has now been found that the use of thymosin $\alpha_1$ in conjunction with the administration of antineoplastics (chemotherapeutic agents) significantly improves the cancer patient's quality of life by reducing nausea, vomiting, loss of appetite, inability to sleep, decline in overall feeling, reduction in daily activity, fatigue and depression. The administration of thymosin $\alpha_1$ does not appear to result in any side effects.

The mechanism by which thymosin $\alpha_1$ acts to improve the patient quality of life is not yet known. Without being bound to any particular theory, one possibility may relate to the apparent ability of thymosin $\alpha_1$ to block neurotransmitter receptors. It is believed that most chemotherapeutic agents activate the chemoreceptor trigger zone (CTZ) and that the CTZ chemotherapy interaction triggers the release of neurotransmitters that activate the vomiting center. CTZ neurotransmitters that are thought to cause emesis include but are not limited to, dopamine, serotonin, histamine, norepinephrine, apomorphine, neurotensin, vasoactive intestinal polypeptide (VIP). In vitro studies, have shown that thymosin $\alpha_1$ has a VIP receptor binding effect. This may explain why thymosin $\alpha_1$ can control vomiting in patients whose vomiting could not be controlled by 5-HT blockers.

The increase in quality of life may be due to thymosin $\alpha_1$'s ability to control GI adverse effects like nausea and vomiting through the above described VIP receptor blocking effect or it could be the result of a reduction of low grade, clinically undetectable infections or some combination thereof.

In one embodiment of the present invention, the thymosin $\alpha_1$ is administered prior to the administration of the chemotherapy. The thymosin $\alpha_1$ may be administered on a single day or be administered on several days prior to the chemotherapy.

In another embodiment of the invention, the thymosin $\alpha_1$ is administered following the administration of the antineoplastic agent. In this embodiment, the thymosin $\alpha_1$ may be administered once or several times prior to the chemotherapy. This administration may take place on a single day or on a series of days prior to the administration of the antineoplastic agent.

In another embodiment of the invention, thymosin $\alpha_1$ is administered prior to and subsequent to the administration of the antineoplastic agent. This administration may take place on one or multiple days prior to and one or multiple days subsequent to the chemotherapy.

In one preferred embodiment, thymosin $\alpha_1$ is administered to cancer patients once each day on four days immediately preceding the administration of the antineoplastic agent and once on day 2 and on day 4 following chemotherapy.

T$\alpha_1$ can be administered in any suitable way, such as by injection, infusion, or transcutaneously. Other methods of administration may also be possible, such as orally as a liquid or solid dosage form. In preferred embodiments $T\alpha_1$ is injected.

Thymosin $\alpha_1$ may be administered at any suitable dosage level, e.g., within a range of about 0.1–3 mg. In preferred embodiments, thymosin $\alpha_1$ is administered via injection at a dosage of about 1.6 mg s.c.

Thymosin $\alpha_1$ can be administered to reduce side effects of any suitable antineoplastic agents, including one or more antineoplastic agent selected from the group consisting of alkylating agents (e.g., nitrogen mustards), antimetabolites (e.g., pyrimidine analogs), radioactive isotopes (e.g., phosphorous and iodine), hormones (e.g., estrogens and adrenocorticosteroids), miscellaneous agents (e.g., substituted ureas) and natural products (e.g., vinca alkyloids and antibiotics). Examples of such anitneoplastic agents include but are not limited to the following:

Adjunct Antineoplasic Therapy
- Aloprim™ for Injection
- Anzemet® Injection
- Anzemet® Tablets
- Aredia® for Injection
- Didronel® I.V. Infusion
- Diflucan® Tablets, Injection, and Oral Suspension
- Epogen® for Injection
- Ergamisol® Tablets
- Ethyol® for Injection
- Kytril® Injection
- Kytril® Tablets
- Leucovorin Calcium for Injection
- Leucovorin Calcium Tablets
- Leukine®
- Marinol® Capsules
- Mesnex® Injection
- Neupogen® for Injection
- Procrit® for Injection
- Salagen® Tablets
- Sandostatin® Injection
- Zinecard® for Injection
- Zofran® Injection
- Zofran® ODT™ Orally Disintegrating Tablets
- Zofran® Oral Solution
- Zofran® Tablets
- Zyloprim® Tablets Alkylating Agents
- Myleran® Tablets
- Paraplatin® for Injection
- Platinol® for Injection
- Platinol-AQ® Injection
- Thioplex® for Injection Nitrogen Mustards
- Alkeran® for Injection
- Alkeran® Tablets
- Cytoxan® for Injection
- Cytoxan® Tablets
- Ifex® for Injection
- Leukeran® Tablets
- Mustargen® for Injection Nitrosoureas
- BiCNU®
- CeeNU®
- Gliadel® Wafer
- Zanosar® Sterile Powder Antibiotics
- Adriamycin® PFS/RDS for Injection
- Blenoxane®
- Cerubidine® for Injection
- Cosmegen® for Injection
- DaunoXome®
- Doxil® Injection
- Doxorubicin Hydrochloride for Injection, USP
- Idamycin PFS Injection
- Mithracin® for Intravenous Use
- Mutamycin® for Injection
- Nipent® for Injection
- Novantrone® for Injection
- Rubex® for Injection
- Valstar™ Sterile Solution for Intravesical Instillation Antimetabolites
- Cytosar-U® Sterile Powder
- DepoCyt™ Injection
- Fludara® for Injection
- Sterile FUDR
- Leustatin® Injection
- Methotrexate Sodium Tablets, Injection, for Injection and LPF® Injection
- Purinethol® Tablets
- Thioguanine Tablets, Tabloid® Brand
- Xeloda® Tablets Hormonal Agonists/Antagonists
Androgens
- Android® Capsules
- Niladron® Tablets
- Teslac® Tablets
- Testred® Capsules Antiandrogens
- Casodex® Tablets
- Eulexin® Capsules Antiestrogens
- Arimedex® Tablets
- Fareston® Tablets
- Femara™ Tablets
- Nolvadex® Tablets Estrogen & Nitrogen Mustard Combination
- Emcyt® Capsules Estrogens
- Estrace® Tablets
- Estinyl® Tablets
- Estratab® Tablets
- Premarin® Tablets Gonadotropin Releasing Hormone (GNRH) Analogues
- Lupron® Depot
- Lupron® Injection
- Zoladex®

Progestins
   Depo-Provera® Sterile Aqueous Suspension
   Megace® Tablets
Immunomodulators
   Ergamisol® Tablets
   Proleukin® for Injection
Miscellaneous Antineoplastics
   Camptosar® Injection
   Celestone® Soluspan® Suspension
   DTIC-Dome®
   Elspar® for Injection
   Etopophos® for Injection
   Etoposide Injection
   Gemzar® for Injection
   Herceptin® I.V.
   Hexalen® Capsules
   Hycamtin® for Injection
   Hydrea® Capsules
   Hydroxyurea Capsules, USP
   Intron® A for Injection
   Lysodren® Tablets
   Matulane® Capsules
   Navelbine® Injection
   Oncapsar®
   Oncovin® Solution Vials and Hyporets
   Ontak™ Vials
   Proleukin® for Injection
   Rituxan™ for Infusion
   Rituxan® I.V.
   Roferon®-A Injection
   Taxol® Injection
   Taxotere® for Injection Concentrate
   TheraCys®
   Tice® BCG Vaccine, USP
   Velban® Vials
   VePesid® Capsules
   VePesid® for Injection
   Vesanoid® Capsules
   Vumon® for Injection
Photosensitizing Agents
   Photofrin® for Injection
Skin and Mucus Membrane Agents
   Efudex® Cream
   Efudex® Topical Solution
   Fluoroplex® Topical Cream
   Fluoroplex® Topical Solution The invention is illustrated by the following Example, which is not intended to be limiting.

EXAMPLE 1

Method: A randomized crossover open label trial was performed. A total of sixty patients, twenty with lung cancer, twenty with gastric cancer and twenty with breast cancer were studied during two complete cycles of chemotherapy. All patients were randomized into two groups. In group 1, patients received chemotherapy with thymosin $\alpha_1$ in the first cycle, and without thymosin $\alpha_1$ in the second cycle. While patients in group 2 received chemotherapy without thymosin $\alpha_1$ in the first cycle, and with thymosin $\alpha_1$ in the second cycle. The patients were treated as follows:

Twenty lung cancer patients were treated with 100 mg of Etoposide IV on days 1–5 and 40 mg of Cisplatin I.V. on days 1–3 in a 21 day cycle.

Twenty gastric cancer patients were treated with 100 mg of Etoposide IV on days 1–5, 30 mg/m² Calcium Leucovorin I.V. on days 1–5 and 500 mg/m² 5-Fluorouricil (5-FU) I.V. on days 1–5.

Twenty breast cancer patients were treated with 5-Fluorouricil 500 mg/m², Adriamycin I.V. 30 mg/m² I.V. on day 1 and cyclophosphamide 500 mg/m² I.V. on day 1.

A mild anti-emetic consisting of 20 mg metoclopamide, I.M. and 5 mg Dexamethasone I.V. were given to all patients on days 1–5. All subjects on thymosin received six injections of 1.6 mg s.c. T$\alpha_1$ on each of the four days immediately preceding the chemotherapy and on days two and four following chemotherapy. All patients who have completed the two cycles of chemotherapy, then were reallocated into two cohorts, A and B. Cohort A are patients with T$\alpha_1$, and Cohort B are patients without T$\alpha_1$.

Analysis: Quality of life was analyzed using a scored scale for (1) loss of appetite, (2) loss of sleep, (3) fatigue, (4) reduction in daily activity, (5) decline in overall feeling, (6) depression and (7) nausea and vomiting. Maximum total score was 35 points.

Results: A comparison between cycles (with T$\alpha_1$ and without T$\alpha_1$) was performed. The addition of T$\alpha_1$ to chemotherapy cycles significantly increases the quality of life scores compared with cycles without T$\alpha_1$.

| Side Effects | |
|---|---|
| Loss of Appetite | 4.33 vs. 3.99 p = 0.0001 |
| Loss of Sleep | 4.41 vs. 4.10 p = 0.002 |
| Fatigue | 4.05 vs. 3.70 p = 0.0001 |
| Reduction in Daily Activity | 4.12 vs. 3.84 p = 0.0001 |
| Decline in Overall Feeling | 4.32 vs. 3.94 p = 0.0001 |
| Depression | 4.01 vs. 3.72 p = 0.003 |
| Nausea and Vomiting | 4.29 vs. 3.93 p = 0.001 |

Nausea and vomiting classified according to WHO criteria:

| Group | n | Grade 0 | Gr. 1 | Gr. 2 | Gr. 3 | Gr. 4 | P value |
|---|---|---|---|---|---|---|---|
| A (with T$\alpha_1$) | 54 | 7/55 | 33 | 13 | 1 | 0 | P < 0.0005 |
| B (Without T$\alpha_1$) | 53 | 4/53 | 19 | 19 | 11 | 0 | |

Conclusion: Adding T$\alpha_1$ to chemotherapy significantly improves patient quality of life.

What is claimed is:

1. A method of reducing side effects of chemotherapy in a cancer patient, said side effects being selected from the group consisting of loss of appetite, loss of sleep, fatigue, reduction in daily activity, decline in overall feeling, depression, nausea and vomiting and combinations of said side effects, comprising administering to a cancer patient thymosin $\alpha_1$ (T$\alpha_1$), said T$\alpha_1$ being administered prior to administration to said patient of at least one chemotherapy agent selected from the group consisting of allopurinol sodium, dolasetron mesylate, pamidronate disodium, etidronate, fluconazole, epoetin alfa, levamisole HCL, amifostine, granisetron HCL, leucovorin calcium, sargramostim, dronabinol, mesna, filgrastim, pilocarpine HCL, octreotide acetate, dexrazoxane, ondansetron HCL, ondansetron, busulfan, carboplatin, cisplatin, thiotepa, melphalan HCL, melphalan, cyclophosphamide, ifosfamide, chlorambucil, mechlorethamine HCL, carmustine, lomustine, polifeprosan 20 with carmustine implant, streptozocin, doxorubicin HCL, bleomycin sulfate, daunirubicin HCL, dactinomycin, daunorucbicin citrate, idarubicin HCL, plimycin, mitomycin, pentostatin, mitoxantrone, valrubicin, cytarabine, fludarabine phosphate, floxuridine, cladribine, methotrexate, mercaptipurine, thioguanine, capecitabine, methyltestosterone, nilutamide, testolactone, bicalutamide, flutamide, anastrozole, toremifene citrate, tamoxifen, estramustine phosphate sodium, ethinyl estradiol, estradiol, esterified estrogens, conjugated estrogens, leuprolide acetate, goserelin acetate, medroxyprogesterone acetate, megestrol acetate, levamisole HCL, aldesleukin, irinotecan HCL, dacarbazine, asparaginase, etoposide phosphate, gemcitabine HCL, trastuzumab, altretamine, topotecan HCL, hydroxyurea, interferon alfa-2b, mitotane, procarbazine HCL, vinorelbine tartrate, *E. coli* L-asparaginase, Erwinia L-asparaginase, vincristine sulfate, denileukin diftitox, aldesleukin, rituximab, interferon alfa-2a, paclitaxel, docetaxel, BCG live (intravesical), vinblastine sulfate, etoposide, tretinoin, teniposide, porfimer sodium, fluorouracil, betamethasone sodium phosphate and betamethasone acetate, letrozole, etoposide citrororum factor, folinic acid, calcium leucouorin, 5-fluorouricil, adriamycin, cytoxan, and diamino dichloro platinum, said chemotherapy agent in combination with thymosin $\alpha_1$ being administered in an amount effective to reduce said side effects of chemotherapy in said patient.

2. The method of claim 1 wherein said $T\alpha_1$ also is administered subsequent to said chemotherapy agent.

3. The method of claim 1 wherein said $T\alpha_1$ is administered on each of a plurality of days prior to said chemotherapy agent.

4. The method of claim 1 wherein a single administration of $T\alpha_1$ is administered one day immediately prior to administration of said chemotherapy agent.

5. The method of claim 1 wherein a single administration of $T\alpha_1$ is administered on each of two days immediately prior to administration of said chemotherapy agent.

6. The method of claim 1 wherein a single administration of $T\alpha_1$ is administered on each of three days immediately prior to administration of said chemotherapy agent.

7. The method of claim 1 wherein a single administration of $T\alpha_1$ is administered on each of four days immediately prior to administration of said chemotherapy agent.

8. The method of claim 1 wherein said chemotherapy agent is selected from the group consisting of etoposide citrororum factor, folinic acid, calcium leucouorin, 5-fluorouricil, adriamycin, cytoxan, diamino dichloro platinum and combinations of said chemotherapy agent.

9. The method of claim 2 wherein a single administration of $T\alpha_1$ is administered one day immediately subsequent to administration of said chemotherapy agent.

10. The method of claim 2 wherein a single administration of $T\alpha_1$ is administered on each of two days immediately subsequent to said administration of said chemotherapy agent.

11. The method of claim 2 wherein $T\alpha_1$ is administered on a plurality of days prior to and subsequent to the administration of said chemotherapy agent.

12. The method of claim 2 wherein a single administration of $T\alpha_1$ is administered one day immediately prior to and one day immediately subsequent to administration of said chemotherapy agent.

13. The method of claim 2 wherein a single administration of $T\alpha_1$ is administered on each of two days immediately days prior to and two days immediately subsequent to the administration of said chemotherapy agent.

14. The method of claim 1 wherein $T\alpha_1$ is administered at a dosage within a range of about 0.1–3.2 mg.

15. The method of claim 1 wherein $T\alpha_1$ is administered at a dosage of about 1.6 mg.

* * * * *